United States Patent [19]
Berthiaume et al.

[11] Patent Number: 5,160,733
[45] Date of Patent: Nov. 3, 1992

[54] CONDITIONING COMPOSITIONS WITH PERFLUOROPOLYMETHYLISO-PROPYLETHERS

[75] Inventors: Marianne Berthiaume, Waterbury; Janusz Jachowicz, Bethel, both of Conn.

[73] Assignee: Clairol Inc., New York, N.Y.

[21] Appl. No.: 695,672

[22] Filed: May 6, 1991

[51] Int. Cl.$^5$ .............................. A61K 7/075
[52] U.S. Cl. ........................ 424/71; 424/70
[58] Field of Search ................... 424/70, 71

[56] References Cited

U.S. PATENT DOCUMENTS

| | | | |
|---|---|---|---|
| 4,591,610 | 5/1986 | Grollier | 424/70 |
| 4,880,620 | 11/1989 | Vanlaberghe et al. | 424/70 |
| 4,915,938 | 4/1990 | Zawadzki | 424/70 |
| 5,087,733 | 2/1992 | Deppert et al. | 424/72 |
| 5,093,023 | 3/1992 | Pantini et al. | 424/70 |

*Primary Examiner*—Thurman K. Page
*Assistant Examiner*—D. Colucci
*Attorney, Agent, or Firm*—Morton S. Simon

[57] ABSTRACT

Hair conditioning compositions containing a perfluoropolyether and an amino functional silicone, in accordance with the invention, afford prolonged conditioning effect i.e. reduction in flyaway and interfiber friction, which effect lasts through multiple shampooings.

14 Claims, No Drawings

CONDITIONING COMPOSITIONS WITH PERFLUOROPOLYMETHYLISOPROPYLETHERS

FIELD OF THE INVENTION

The present invention relates to conditioning compositions containing a perfluoropolyether, particularly Fomblin ® HC and a conditioning agent selected from the group consisting of amino-functional silicones and/or isothiuronium compounds.

DESCRIPTION OF THE RELATED ART

Fluorinated polyethers and perfluoropolyethers are well-known in the art of cosmetics. They are used as active ingredients in, as well as components of, cosmetic compositions.

JP 63.107911 details the use of perfluoropolyethers of the formula $F(C_3F_6O)C_2F_5$ in skin and hair care compositions to improve the moisturizing quality of said compositions. This Japanese reference merely discloses conventional components such as vaseline, olive oil and polyethyleneglycol in combination with perfluoroether.

U.S. Pat. No. 4,044,121 discloses the incorporation of certain perfluoropolyethers into hair spray products. The perfluoropolyethers have the formula $R_fQ(XCO)A(COOZ)$, wherein $R_f$ is a monovalent, fluorinated, saturated, aliphatic radical having 3-20 carbon atoms; Q is a divalent linking group; X is —O— or —NR— wherein R is hydrogen or alkyl having 1-14 carbon atoms; A is phenylene containing only hydrogen substituents on the aromatic carbon or phenylene, wherein 1 or more of the hydrogens have been replaced by chlorine, bromine, alkyl having 1-4 carbon atoms or combinations thereof; and Z is hydrogen or a cation selected from the group consisting of $NH_4^+$, $Na^+$, $K^+$, $Li^+$, a protonated alkylamine or alkanolamine having 1-6 carbon atoms and quaternized forms of said amines. The use of the above-specified components results in improved efficiency in soil resistance and curl retention.

U.S. Pat. No. 3,959,462 discloses a process for keeping hair cleaner longer by applying to the hair a perfluoroether of the formula:

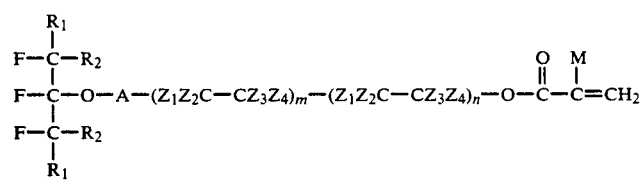

wherein $R_1$ and $R_2$ are each F, Cl, alkyl or haloalkyl groups or when taken together are alkylene or haloalkylene groups forming a cycloaliphatic structure, which $R_1$ and $R_2$ groups may contain from 1 to 9 carbon atoms and which halogen atoms, if any, have an atomic weight not exceeding 79.91 with the proviso that no more than two of the $R_1$ and $R_2$ groups are alkyl groups, and no more than three of the $R_1$ and $R_2$ groups are haloalkyl.

A is a radical of the formula —$CFR_3$—$CR_4R_5$— in which $R_3$ and $R_4$ are independently selected from the group consisting of F and H, and $R_5$ is selected from the group consisting of H, F, Cl, Br and perfluoralkyl. $Z_1$, $Z_2$, $Z_3$ and $Z_4$ may each be selected from the group consisting of H, F, Cl and Br, provided that $Z_1$, $Z_2$, $Z_3$ and $Z_4$ do not include more than 2 chlorine atoms or 1 bromine atom when at least two members of the group $Z_1$, $Z_2$, $Z_3$ and $Z_4$ are H or F, the remaining two members may each be a perhalomethyl group having the formula —$C(X_a)_3$, wherein $X_a$ is a halogen atom having an atomic weight not exceeding 79.91.

When $Z_1$ and $Z_3$ are each H or F, each of $Z_2$ and $Z_4$ may additionally be selected from the group consisting of —$CF_2X_B$—$Y_1$, —$OY_2$—$Y_1$—$Y_3$ and —O—$Y_4$, wherein $X_b$ is an alkyl radical having from 1-8 carbon atoms, or a haloalkyl radical having from 1-8 carbon atoms, in which haloalkyl radical the halogen atoms have an atomic weight not exceeding 79.91; $Y_1$ is a saturated divalent alkylene bridging group or a saturated haloalkylene bridging group in which the halogen atoms have atomic weights not exceeding 79.91; $Y_2$ is a member selected from the group consisting of H and alkyl; $Y_3$ is aryl and $Y_4$ is alkyl; $Z_3$ and $Z_4$ or $Z_1$ and $Z_3$ may be joined together to form a cycloaliphatic ring system; M is a member selected from the group consisting of H or $CH_3$; m is an integer from 1-75 and n is an integer from 0-75, with the proviso that the terminal carbon atom in the —($Z_1Z_2C$—$CZ_3Z_4$)— group which is bonded to the —O— atom is additionally bonded to 2 hydrogen atoms. The $Z_1$, $Z_2$, $Z_3$ and $Z_4$ substituents, as indicated above, are independently selected. Each of the $Z_1$, $Z_2$, $Z_3$ and $Z_4$ substituents may differ from one another. Moreover, each of these substituents in the —($Z_1Z_2C$—$CZ_3Z_4$)$_m$— moiety may differ from the $Z_1$, $Z_2$, $Z_3$ and $Z_4$ substituents present in the —($Z_1Z_2C$—$CZ_3Z_4$)$_n$ moiety.

U.S. Pat. No. 4,880,620, discloses the use of certain perfluorinated polyethers to slow down the flow of sebum, thus imparting an oleofugic effect to the hair. The perfluorinated polyethers conform to the formula:

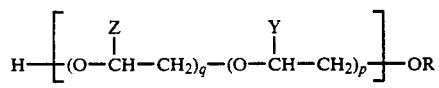

where in R is $H(CH_2)_m$—, $F(CF_2)_n$—$CH_2$—, $F(CF_2)_n$—$CH_2$—$CH_2$—, or $H(CF_2)_n$—$CH_2$—, wherein m and n represent an integer from 1 to 16, or a group of the formula $A(CF_2)_n$—$(CH_2)_m$— wherein A represents hydrogen or fluorine, m is an integer from 1-16, n is an integer from 0-16, with the proviso that if n is O, A is hydrogen and if n is 1-16, m is 1, 2 or 3.

Y rpresents $C_xF_{2x+1}$, $C_xF_{2x+1}$—$CH_2$—, $C_xF_{2x+1}CH_2$—O—$CH_2$—, $C_xF_{2x+1}(CH_2)_2$—O—$CH_2$—, or $HC_xF_{2x}CH_2$—O—$CH_2$—, wherein x is an integer from 6-10, Z represents —$CH_2OH$, and p and q each independently represent an integer or decimal number ranging from 0.5 to 30.

U.S. Pat. No. 4,803,067 discloses perfluoropolyether containing compositions for cosmetics and dermatology. The perfluoropolyethers conform to the formula $CF_3O-(C_3F_6O)_m(CFXO)_n-CF_2Y$, wherein X and Y are —F or —$CF_3$ and m and n are integers, the m/n ratio ranging from 5 to 40.

Fomblin® HC is a perfluoropolymethylisopropylether corresponding to the formula:

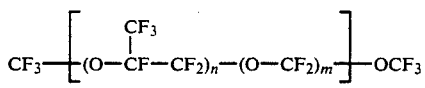

wherein n/m=20–40, and having a molecular weight ranging from 1500 to 6600. This product is commercially available under the tradenames Fomblin® HC/04, HC/25 and HC/R, and is sold by Montefluos (distributed by Brooks Industries). Fomblin® HC is widely used in cosmetics, since it possesses such valuable properties as being hydrophobic, lipophobic and homophobic; being vapor permeable; imparting lubricity; aiding in formation of stable emulsions; and the like.

U.S. Pat. No. 4,803,067 describes compositions for cosmetics and dermatology comprising Fomblin® dispersed in oil/water or water/oil emulsions.

Articles disclosing the properties and use of Fomblin® HC include: Visca et al "Fluorinated oils in model cosmetic emulsions", 15th international I.F.S.C.C. Congress, London, September '88; Pantini et al, "Fomblin® HC," Technol-Chim., 8(3), 126, (1989); "Cosmetic formulations containing Fomblin® HC", Cosmet. and Toiletries, (104), pp 72–99, (1989); Pantini et al "Perfluoropolyethers for Cosmetics", Drug Cosmet. Ind., 143 (3), 34, (1988); Pantini et al "Perfluoropolyethers: Multiphase emulsions of three immiscible liquids", Chemspec. Europe 1988 symposium.

A hair conditioner containing Fomblin® HC/04 and dimethicone was disclosed at the I.F.S.C.C. meeting, Oct. 8–11, 1990, New York. However, the improved combing results obta ined with this conditioning composition are not long-lasting. The reduction in interfiber friction is almost completely eliminated after two shampooings.

Cationic surfactants and cationic polymers have been widely used in cosmetic formulations. Conditioning treatments containing low molecular weight quaternary compounds ("quats"), are known to improve combability of hair while lowering triboelectric charging. These materials are not durable, since the adsorbed material is easily removed upon exposure to detergents, i.e. during shampooing. Incorporation of cationic polymers into conditioning products provides more substantive hair surface modification, lasting through several shampooings. In order for these treatments to improve combability, however they require formation of a complex with the anionic detergents. Another problem encountered with polymeric conditioning treatments is the generation of static charge, or fly away, leaving the hair unmanageable.

Silicone oils and emulsions based on same are quite popular in conditioning formulations. Although these materials are usually incorporated into instant or daily use conditioners, with the exception of the volatile silicones, they have been reported to last through several shampooings. While it is true tha silicones are notorious for producing substantial reductions in combing forces, they are also known for imparting unacceptable triboelectric characteristics to the hair. This problem may be solved by incorporating antistatic agents into the formulation; however, these agents are easily removed by shampooing, whereas the silicones remain, leaving the hair conditioned but unmanageable. Reapplication of the product containing the antistatic agent may lead to an undesirable "build up".

Certain isothiuronium-containing compounds have been discovered to be useful as hair conditioners, however they have also been found to impart fly away to the hair.

None of the aforementioned publications teaches or suggests the unexpected synergistic effects on the conditioning effect of incorporation of a perfluoropolyether into compositions containing aminofunctional silicone(s) and/or isothiuronium compound(s).

SUMMARY OF THE INVENTION

One object of the invention is to provide long-lasting conditioning compositions comprising:
a) 0.1–5% of perfluoropolyether;
b) 1–10.0% of a conditioning agent selected from the group consisting of certain amino-functional silicones and/or certain isothiuronium compounds; and
c) a cosmetically acceptable carrier.

Another object of the present invention is to provide a process for conditioning hair, which comprises applying thereto a conditioning composition as described hereinabove.

DETAILED DESCRIPTION OF THE INVENTION

Accordingly, the present invention provides a long-lasting conditioning composition comprising, by weight, based on the total weight of the composition:
a) 0.1–5% of perfluoropolyether;
b) 1–10.0% of a conditioning agent selected from the group consisting of: amino-functional silicones having an amine-content ranging from 0.1 to 1.0 equivalent, the preferred range being from 0.3 to 0.8 equivalent, and isothiuronium compounds, which are those compounds containing one or more of the functional group

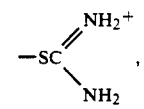

mixtures thereof; and
c) a cosmetically acceptable carrier.

The amino-functional silicones are the silicones corresponding to the formula:

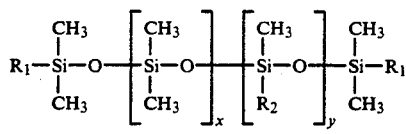

wherein:
$R_1$ is methyl, hydroxy, or methoxy;
$R_2$ is $(CH_2)_3NH(CH_2)_2NH_2$, or $CH_2CH(CH_3)CH_2NH(CH_2)_2NH_2$;
wherein x and y are integers such that the molecular weight of the polymer is from 400–500,000, with the ratio of x/y being such that the amine content ranges from 0.1 to 1.0 equivalent.

The amine content is defined as the normal (N) concentration of amine containing units. It ranges from 0.1 to 1.0 amine equivalent. The preferred amine content ranges from 0.3 to 0.8 equivalent.

Particularly preferred amino-functional silicones are the following:

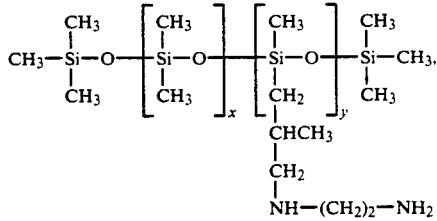
1.

such as Dow Corning Q2-8220 or Dow Corning Q2-8075 fluids;

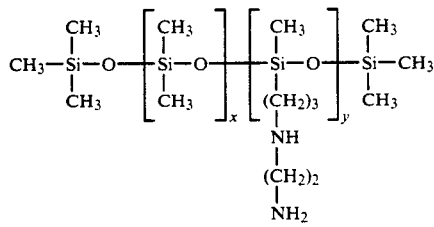
2.

such as General Electric SF 1708.

The isothiuronium conditioning agents contain one or more of the functional groups of the formula:

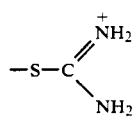

The isothiuronium conditions encompassed by the present invention include isothiuronium compounds of the following formulas, and mixtures thereof:

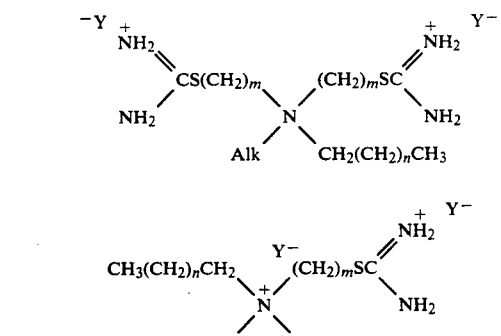

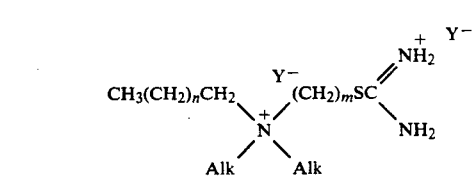

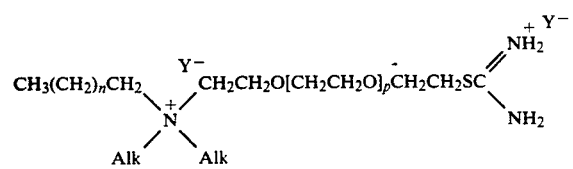

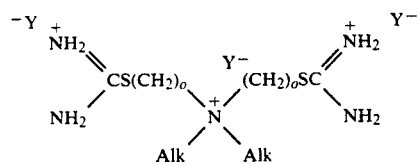

wherein

Alk is an alkyl group containing from 1 to 4 carbon atoms;

$Y^-$ is an anion;

n is an integer from 10 to 24;

m is an integer from 1 to 4;

o is an integer from 8 to 11;

p is an integer from 0 to 20;

with the proviso that the total number of carbon atoms in the cation is not greater than 28; and further compounds wherein the long alkyl chain is interrupted with a phenylene group so that the structure of the interrupted alkyl chain is represented by the formula:

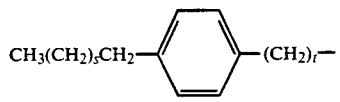

wherein s is an integer of from 8 to 17 and t is an integer from 1 to 5;

Further isothiuronium compounds are those represented by the following formulas:

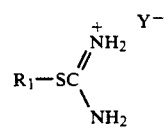

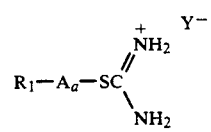

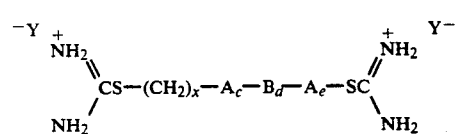

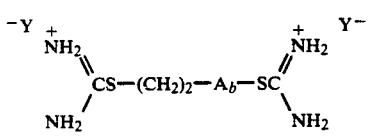

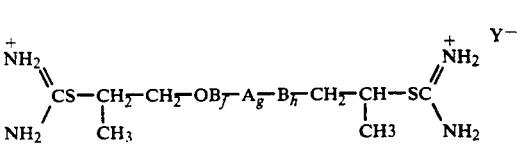

-continued

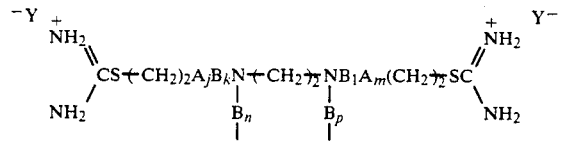

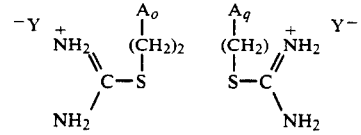

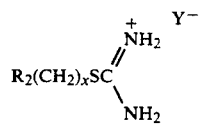

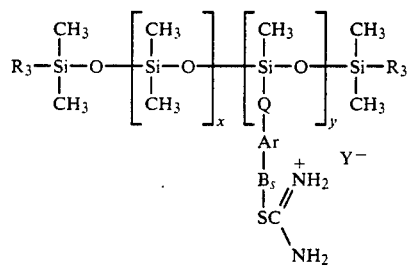

wherein:
R₁ is an alkyl or arylalkyl group, wherein the alkyl moiety contains from 12 to 24 carbon atoms;
R₂ is a perfluoroalkyl group having from 4 to 16 carbon atoms;
R₃ is methyl, hydroxy, or methoxy;
A is an ethoxy group;
B is a propoxy group;
Y⁻ is an anion, and Br⁻, Cl⁻ or I⁻
Q is an alkylene group having from 2 to 5 carbon atoms;
a through s are integers designating, as the case may be, the degree of ethoxylation and/or propoxylation;
v is an integer from 5 to 500;
w is an integer from 5 to 200; and
n is an integer from 0 to 4.

Specific examples of isothiuronium compounds useful in the present invention are:

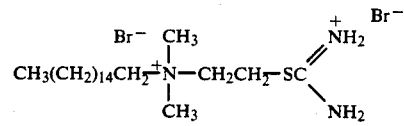

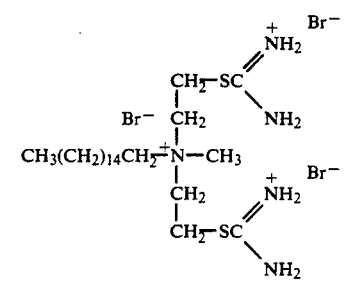

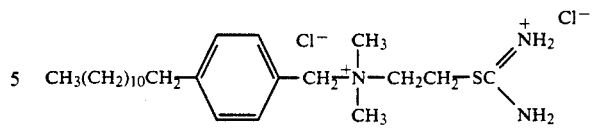

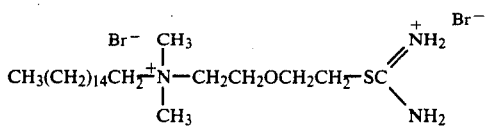

A mixture of compounds of the formula:

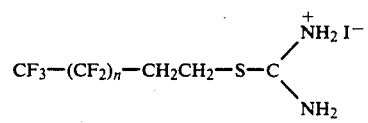

wherein n is 3 to 13

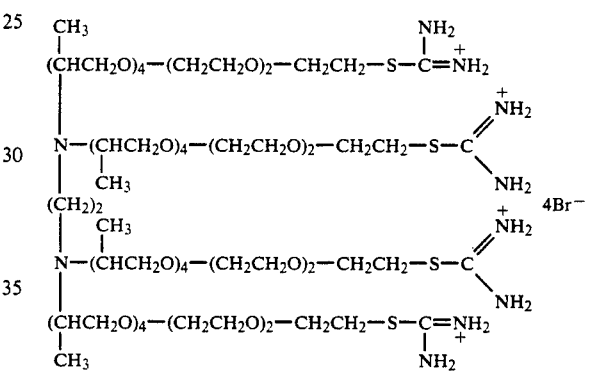

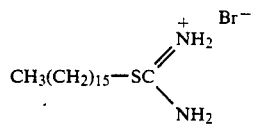

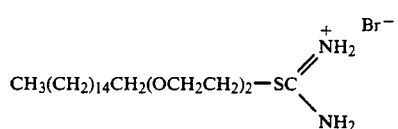

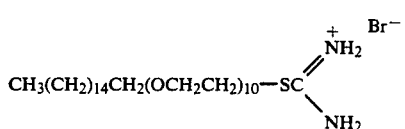

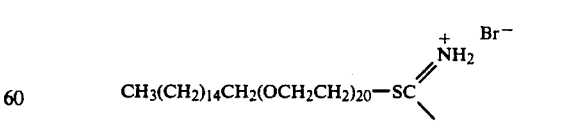

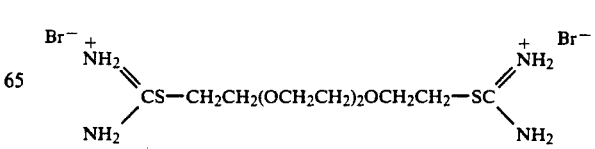

*-continued*

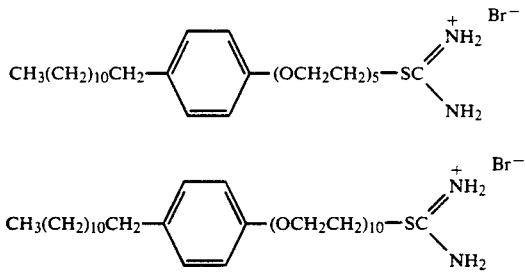

The compound of the formula:

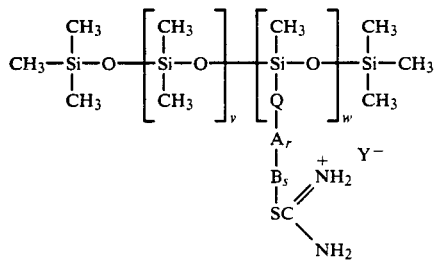

wherein: v is an integer of 5 to 500, w is an integer of about 5 to 200, and r and s are integers with values such that the average molecular weight is from about 1000 to about 100,000.

Preferred perfluoropolyether compounds useful in the present invention include perfluoropolymethylisopropylether, available under the trade name Fomblin ® HC, and the polyhexafluoroisopropylether described in JP 63.107911 and available under the trade name Krytox. The perfluoropolymethylisopropyl ether is most preferred.

The ratio of perfluoropolyether to conditioning agent may vary from 1:1 to 1:100. A ratio of from 1:1 to 1:10 is preferred.

Any suitable cosmetically acceptable vehicle employed in the cosmetic art for hair products may be utilized for the compositions of the present invention. Water will ordinarily constitute the major component of the conditioning composition of the present invention. The amount of water employed can vary widely depending on the types and quantity of adjuvants or additives contained in the composition. Thus, based on the total weight of the conditioning composition, water may constitute from 40 wt.% to 99 wt.% of the composition. More often, it constitutes from 70 wt.% to 95 wt.%, on the same weight basis.

It is often advantageous to include in the present conditioning composition an organic solvent or solvent system which helps solubilize the adjuvants and additives contained therein. A number of organic solvents are known in the art that are useful for that pu rpose. These include alcohols (particularly alkyl alcohols of 1-6 carbon atoms), glycols of up to about 10 carbons, and glycerol. Preferred solvents are polyhydric alcohols, such as ethylene glycol, propylene glycol, sorbitol, etc.

The conditioning compositions of the present invention may also contain other conventional adjuvants or additives, commonly found in conditioning compositions. Included in these are surface active agents, thickening agents, chelating agents, humectants, preservatives, perfumes, and the like.

The surface active emulsifying agents are typically water soluble, or may be water dispersible, and include anionic, nonionic or cationic surface active agents. These surfactants may be present in an amount from 0.5 wt.% to 30 wt.%, based on the total weight of the composition. Various types of such emulsifying surfactants are the alkoxylated alcohols, the polyethylene glycol ethers of long alkyl chain alcohols, fatty alcohols, and the like. Specific suitable examples are: isolaureth-6, cetyl alcohol, and glycerol monostearate.

Emulsion stabilizers may also be included in the composition. They may be present in an amount from 0.5 wt.% to 20 wt.%, based on the total weight of the composition. Examples of suitable emulsion stabilizers include cetyl alcohol and hydroxyethylcellulose.

Cleansing agents may also be added to the composition. They may be present in an amount from 0.5 wt.% to 10 wt.%, based on the total weight of the composition. A suitable example is octoxynol-40.

Preservatives may also be included in the conditioning composition. They may be present in an amount from 0.1 wt.% to 2.0 wt.%, based on the total weight of the composition. Examples of suitable preservatives are: DMDM hydantoin, methyl and propylparaben and 2-phenoxyethanol.

Humectants may also be included in the conditioning composition. They may be present in an amount from 0.1 wt.% to 10.0 wt.%, based on the total weight of the composition. Sorbitol and glycerol are examples of suitable humectants.

The pH of the composition may vary from 3.5 to 9.0. A preferred range is pH 4 to 8. pH adjusting agents which may be incorporated in the present composition include: citric acid, sorbic acid, phosphoric acid, hydrochloric acid, sodium hydroxide, potassium hydroxide, ammonium hydroxide, etc.

The conditioning composition of the present invention may be prepared by conventional methods used in the art. The following general procedure is preferred: Prepare a mixture of the oil phase components and a mixture of the water phase components. Separately heat the water and oil phases to 65°-70° C. Slowly add the oil phase to the water phase, with stirring. Continue the stirring through cool down (~30° C.). When cool, add fragrances, if any.

The conditioning composition of the present invention can be applied to the hair by conventional techniques known in the art. Illustratively, they can be poured over the hair or applied with a brush, sponge, or other means of contact, until the hair is properly impregnated. The time of contact of the conditioning composition can vary from 0.5 minute to 30 minutes. The composition is preferably applied at ambient temperature.

The following examples are illustrative of the present invention and should not be considered as limiting the scope of same. It should be noted that unless indicated otherwise all percentages are percent by weight based on the total weight of the composition.

EXAMPLE 1

Compositions A through E are prepared by mixing the oil and water phases in accordance with the previously discussed general procedure. It should be noted that in the formulation components of the various phases are indicated as being: (+), which indicates it is includable as part of the water phase or (−), which indicates it is includable as part of the oil phase.

| Material | Amount (wt. %) |
|---|---|
| − Fomblin ® HC/04 | as indicated below |
| − Silicone oil Q2-8220 | as indicated below |
| + Octoxynol 40 | 2.5% |
| + Isolaureth 6 | 1.0 |
| + Ethylene glycol | 0.5 |
| − Cetyl alcohol | 3.5 |
| − Glyceryl monostearate | 3.5 |
| + Methyl paraben | 0.1 |
| + Propyl paraben | 0.1 |
| + Sorbitol | 5.0 |
| + Glycerol | 2.0 |
| + Water | qs to 100.0 |

| Composition | A-1 | A-2 | B-1 | B-2 | C-1 | C-2 | C-3 | D-1 | D-2 | E-1 | E-2 |
|---|---|---|---|---|---|---|---|---|---|---|---|
| Fomblin ® HC | 0.1 | — | 0.1 | — | 0.5 | — | — | 1.0 | — | 5.0 | — |
| Silicone Oil | 0.1 | 0.2 | 10.0 | 10.1 | 1.5 | 2.0 | 1.5 | 5.0 | 6.0 | 10.0 | 15.0 |
| Ratio | 1:1 | | 1:100 | | 1:3 | | | 1:5 | | 1:2 | |

Two gram tresses of precleaned virgin brown hair were dyed for a period of 30 minutes with a black shade of a commercially available oxidative hair color. The dyed tresses were then rinsed. The rinsed dyed tresses were then treated with test conditioning compositions for a period of 5 minutes. The tresses were then rinsed for 30 seconds under running tap water. Th efficacy and substantivity of the test compositions were evaluated by means of a combing test utilizing an Instron Model 1130, employing a crosshead speed of 10 cm/min. The method of Garcia-Diaz was followed [see J. Soc. Cosm. Sci., 27,379 (1976)].

Test compositions A-1, A-2, B-1, B-2, C-1, C-2, C-3, D-1, D-2, E-1 and E-2 were evaluated. Compositions A-1, B-1, C-1, D-1 and E-1 are compositions in accordance with the present invention.

Compositions A-2, B-2, C-2, D-2 and E-2 are compositions wherein Fomblin ® HC/04 was replaced with the silicone oil, so that the total concentration of active conditioning agents was equivalent in both formulations.

Composition C-3 is a composition wherein Fomblin ® was replaced with water.

Composition 2-A is a composition containing 0.5% Fomblin ® as the sole conditioning agent.

The results, compared to an unconditioned, similarly dyed control, are set forth in the following Table 1. It should be kept in mind that in Table 1 the lower the value, the greater the ease of combing, the lower the interfiber friction, and the greater the conditioning effect.

TABLE 1

| Test Composition | Active(s) | Results of Wet Combing Experiments (g*cm) Number of Shampooings | | | |
|---|---|---|---|---|---|
| | | 0 | 2 | 4 | 8 |
| Uncondi- tioned, Dyed Control | — | 1554 | 3848 | 4324 | 4762 |
| 2-A | 0.5% Fomblin ® | 2001 | 4591 | 4918 | 4935 |
| A-1 | 0.1% Fomblin ® +0.1% Silicone | 1035 | 2169 | 3078 | 4337 |
| A-2 | 0.2% Silicone | 1010 | 2193 | 3472 | 4502 |
| B-1 | 0.1% Fomblin ® +10.0% Silicone | 82 | 224 | 915 | 2176 |
| B-2 | 10.1% Silicone | 484 | 997 | 2524 | 4281 |
| C-1 | 0.5% Fomblin ® +1.5% Silicone | 280 | 1678 | 3499 | 3858 |
| C-2 | 2.0% Silicone | 397 | 2116 | 4034 | 4449 |
| C-3 | 1.5% Silicone | 377 | 2659 | 4048 | 4810 |
| D-1 | 1.0% Fomblin ® | 170 | 898 | 2317 | 4056 |

TABLE 1-continued

| Test Composition | Active(s) | Results of Wet Combing Experiments (g*cm) Number of Shampooings | | | |
|---|---|---|---|---|---|
| | | 0 | 2 | 4 | 8 |
| D-2 | +5.0% Silicone 6.0% Silicone | 256 | 1052 | 3366 | 4352 |
| E-1 | 5.0% Fomblin ® +10.0% Silicone | 76 | 295 | 795 | 1406 |
| E-2 | 15.0% Silicone | 95 | 414 | 922 | 2035 |

Sample 2-A, containing 0.5% Fomblin ®, shows that Fomblin ®, in and of itself, is not an effective conditioning agent. However, when combined with a sufficient amount of one of the conditioning actives of the present invention, small quantities of Fomblin ® produce unexpected synergistic conditioning effects. This is clearly evidenced in the data set forth in Table 1. Moreover, the present inventors found that such synergistic effects were obtained only with the combinations of Fomblin ® and the co-conditioning agents of the present invention.

Referring once again to Table 1, test compositions A-1 and A-2 were found to yield comparable results, and neither of these compositions was effective in reducing combing forces. Composition A-1 contains 0.1% each of Fomblin ® and silicone, while Composition A-2 contains 0.2% silicone only. Thus, it is evident that the amount of silicone required to provide conditioning benefits is larger than 0.1%.

Compositions B-1 and B-2 show that the addition of 0.1% Fomblin ® to 10% silicone is sufficient to produce synergistic conditioning benefits which last through eight shampooings.

The results obtained from compositions C-1, C-2, and C-3 show that the composition containing 2% silicone (C-2) evidences a greater degree of reduced combing force than the composition (C-3) containing 1.5% silicone. But the (C-1) composition containing 1.5% silicone and 0.5% Fomblin ® affords an even greater reduction in combing force.

The data generated in respect of Composition E-1 (5% Fomblin ® and 10% silicone) and composition E-2 (15% silicone) shows that there is still a synergistic effect at the upper limits of the ranges claimed herein (viz 5% Fomblin ® and 10% silicone). These data suggest that the amount of Fomblin ® required to produce a synergistic conditioning effect is from about 0.1–5.0%, while the amount of silicone oil is about 1.0–10.0%. Compositions containing larger amounts of these materials, in the proper ratio, are also expected to offer substantial conditioning benefits, however the hair might be characterized by an unacceptable coated quality. Thus, although such compositions may well afford the desirable conditioning properties of the compositions of the present invention, they would most assuredly be commercially unacceptable.

Dry combing experiments were also performed with compositions C-1, C-3 and 2-A. The results are given in the following Table 2:

TABLE 2

Results of Dry Combing Experiment

| Test Composition | Active(s) | Number of Shampooings | | | | |
|---|---|---|---|---|---|---|
| | | 0 | 1 | 2 | 4 | 8 |
| Unconditioned, Dyed Control | — | 410 | 477 | 556 | 632 | 889 |
| C-1 | 0.5% Fomblin ® +1.5% Silicone | 108 | 268 | 397 | 903* | 731 |
| C-3 | 1.5% Silicone | 277 | 568 | 933 | 935 | 939 |
| 2-A | 0.5% Fomblin ® | 487 | 818 | 876 | 752 | 883 |

*Inconsistency of this high value with the other results is believed to be attributable to entanglement, which frequently occurs in dry combing measurements.

and a strip chart recorder. The results are set forth in the following Table 3:

TABLE 3

Triboelectric Experiments (mV)

| Test Composition | Active(s) | Nature of Comb Material | | | |
|---|---|---|---|---|---|
| | | Nylon | PC | PE | Teflon |
| Unconditioned, Dyed Control | | −18.6 | −21.8 | 40.4 | 52 |
| C-1 | 0.5% Fomblin ® +1.5% Silicone | −15.4 | −16.8 | 17.2 | 35.8 |
| C-3 | 1.5% Silicone | −26.5 | −25.1 | 20 | 36.2 |
| 2-A | 0.5% Fomblin ® | 21.8 | 31.6 | 46.5 | 37.2 |

PC - polycarbonate
PE - polyethylene

The results of Table 3 clearly show the effect of reduction in triboelectric charging for compositions containing Fomblin ® HC in combination with an aminofunctional silicone, even at low concentration.

EXAMPLE 2

Compositions F through I were prepared utilizing the general procedure employed in Example 1.

| Material | Amount (wt %) | | | | | | | | |
|---|---|---|---|---|---|---|---|---|---|
| − Fomblin$^R$ HC | as indicated below | | | | | | | | |
| + Isothiuronium * | as indicated below | | | | | | | | |
| + Hydroxyethylcellulose | 1.0 | | | | | | | | |
| − Cetyl alcohol | 3.5 | | | | | | | | |
| − Glyceryl monostearate | 3.5 | | | | | | | | |
| + Methyl paraben | 0.1 | | | | | | | | |
| + Propyl paraben | 0.1 | | | | | | | | |
| + Water | qs to 100.0 | | | | | | | | |
| Test Composition | F-1 | F-2 | F-3 | G-1 | G-2 | H-1 | H-2 | I-1 | I-2 |
| Fomblin$^R$ | 0.5 | — | — | 0.5 | — | 0.5 | — | 0.4 | — |
| Isothiuronium* | 2 | 2.5 | 2 | 1.0 | 1.5 | 0.5 | 1.0 | 4.0 | 4.4 |
| Ratio of Fomblin$^R$: Isothiuronium | 1:4 | — | — | 1:2 | — | 1:1 | — | 1:10 | — |

*The isothiuronium compound, employed in this Example 2 and in all isothiuronium containing formulations of this application has the structure:

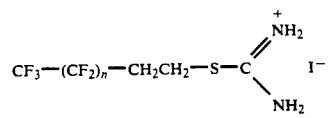

When prepared it separates into two fractions, an ethanol soluble fraction and an ethanol insoluble fraction. One-half of the amount of the isothiuronium compound employed herein was comprised of the ethanol-soluble fraction. The remainder was comprised of the ethanol-insoluble fraction.

The data presented in Table 2 once again confirm that Fomblin ® is not an effective conditioning agent when used alone. The data clearly show that when Fomblin ® is used in combination with silicone, one obtains unexpected and surprising conditioning effects. When hair is treated with a conditioning composition containing only silicone, reduction in interfiber friction is obtained, but such improvement is obviated by shampooing. Incorporation of Fomblin ® into such formulation surprisingly results in hair characterized by lower combing forces even after eight shampooings.

Upon completion of the combing evaluations, hair tresses were retreated with conditioning compositions Cl, and C3, and 2-A for 5 minutes, then rinsed for 30 seconds under running tap water. They were then allowed to equilibrate overnight at 45% relative humidity and at a temperature of 21.C. Then triboelectric measurements were made. The hair tresses were combed 10 times per side, using combs prepared from various polymeric materials. Voltage measurements of surface charge were performed using a Keithley model 2501 static detector attached to a Keithley 610 electrometer The results of combing experiments performed on hair tresses treated with these compositions are presented in Table 4 below.

TABLE 4

Results of Wet Combing Experiments (g*cm)

| Test Composition | Active(s) | Number of Shampooings | | | |
|---|---|---|---|---|---|
| | | 0 | 2 | 4 | 8 |
| Unconditioned, Dyed Control | | 1554 | 3848 | 4324 | 4762 |
| 2-A | 0.5% Fomblin ® | 2001 | 4591 | 4918 | 4935 |
| F-1 | 0.5% Fomblin ® +2% isothiuronium | 276 | 1098 | 1197 | 1400 |
| F-2 | 2.5% isothiuronium | 341 | 1195 | 1426 | 1979 |
| F-3 | 2% isothiuronium | 332 | 1374 | 1402 | 2198 |
| G-1 | 0.5% Fomblin ® +1.0% isothiuronium | 384 | 1050 | 1922 | 3199 |
| G-2 | 1.5% isothiuronium | 612 | 1308 | 2514 | 3493 |
| H-1 | 0.5% Fomblin ® +0.5% isothiuronium | 969 | 1332 | 2249 | 3507 |
| H-2 | 1.0% isothiuronium | 1425 | 1763 | 2678 | 3649 |
| I-1 | 0.4% Fomblin ® +4.0% isothiuronium | 272 | 482 | 948 | 1288 |

TABLE 4-continued

| Test | | Results of Wet Combing Experiments (g*cm) | | | |
|---|---|---|---|---|---|
| | | Number of Shampooings | | | |
| Composition | Active(s) | 0 | 2 | 4 | 8 |
| I-2 | 4.4% isothiuronium | 339 | 676 | 1002 | 1958 |

It can be seen that the test composition containing 2.5% isothiuronium surfactant (F-2) produced a greater reduction in combing forces than did the formulation comprised of 2% isothiuronium surfactant; however, this formulation was not as effective in lowering inter fiber friction as was the composition containing 0.5% Fomblin ® and 2% isothiuronium surfactant (F-1). Test compositions G-2, H-2 and I-2 evidence an improvement in combing ease as compared to the dyed control, supporting the known conditioning benefits of the isothiuronium compounds. Compositions G-1, H-1 and I-1, however, were surprisingly found to offer unexpectedly much greater reductions in interfiber friction (as seen in Table 4) confirming the synergistic interaction between Fomblin ® and the isothiuronium surfactant, in the conditioning of hair. The data indicate that the effective range of isothiuronium surfactant to be included in these Fomblin ® containing conditioning formulations should be from 1.0 to 10.0%. The preferred ratio of Fomblin ® to isothiuronium surfactant should be from 1:1 to 1:10.

Dry combing experiments were also performed with compositions F-1, F-3, and 2-A. The results are presented in the following Table 5.

TABLE 5

| Test Composition | | Results of Dry Combing Experiments (g*cm) | | | | |
|---|---|---|---|---|---|---|
| | | Number of Shampooings | | | | |
| | Active(s) | 0 | 1 | 2 | 4 | 8 |
| Uncondi-tioned, Dyed Control | | 410 | 477 | 556 | 632 | 889 |
| F-1 | 0.5% Fomblin ® +2% isothiuronium | 159 | 203 | 238 | 278 | 309 |
| F-2 | 2.5% isothiuronium | 240 | 327 | 340 | 428 | 492 |
| 2-A | 0.5% Fomblin ® | 487 | 818 | 876 | 752 | 883 |

The data of Table 5 show that initially and after eight shampooings, the test composition containing 0.5% Fomblin ® (2-A) performed essentially as did the unconditioned control.

The test composition (F-2) containing 2.5% isothiuronium surfactant evidenced conditioning even after eight shampooings. However, the test composition (F-1) containing 0.5% Fomblin ® and 2% isothiuronium surfactant surprisingly evidenced close to a 40% greater conditioning effect than did the composition containing 2.5% isothiuronium surfactant (F-2). This is surprising, principally because Fomblin ® evidenced no conditioning effect and the replacement of the hair conditioning isothiuronium surfactant by what is obviously a non-hair conditioning agent such as Fomblin ® would be expected to decrease the conditioning effect of the formulation. Instead a 40% enhancement was surprisingly obtained.

Upon completion of the combing evaluations, the appropriate hair tresses were retreated with the corresponding conditioning test compositions (F-1, F-3 or 2-A) for 5 minutes, then rinsed for 30 seconds under running tap water. They were then allowed to equilibrate overnight at 45% relative humidity, and at a temperature of 21° C., after which time triboelectric measurements were made. The results are presented in the following Table 6.

TABLE 6

| | | Results of Triboelectric Experiments (mV) | | | |
|---|---|---|---|---|---|
| | | Comb Material | | | |
| | Active(s) | Nylon | PC | PE | Teflon |
| Uncondi-tioned, Dyed Control | | −18.6 | −21.8 | 40.4 | 52.0 |
| F-1 | 0.5% Fomblin ® +2% isothiuronium | −25.1 | −22.3 | −21.8 | −17.2 |
| F-3 | 2.0% isothiuronium | −37.2 | −37.2 | −37.2 | −42.8 |
| 2-A | 0.5% Fomblin ® | 21.8 | 31.6 | 46.5 | 37.2 |

Treatment of hair with other fluorocarbon materials, such as the Zonyl ® surfactants (Du Pont) or the Fluorads ® (3M) or the perfluoro-isothiuronium surfactants (see formulation F-3), tend to impart an unacceptable amount of triboelectric charging to the surface of the fibers. It can be seen from Table 6, that incorporation of Fomblin ® into a conditioning formulation reduces the amount of fly-away of the tresses treated with these materials. For all comb types tested, the Fomblin ® containing system (F-1) exhibited lower amounts of triboelectric charging than the blank counterpart.

In summary, upon examination of the data presented in the Tables, several features become obvious:

1) Compositions containing Fomblin ® HC in combination with an aminofunctional silicone oil, an isothiuronium surfactant or a mixture thereof showed a more dramatic reduction in combing forces than did their blank counter-parts for all formulations, in both wet and dry combing experiments.

2) Fomblin ®, by itself, is not an efficacious conditioning agent.

3) Combinations of Fomblin ® with an aminofunctional silicone oil, an isothiuronium surfactant or a mixture thereof results in a surprising and unexpected synergistic conditioning effect, which is durable and withstands multiple shampooings.

4) The conditioning formulations of the present invention do not contribute to an increase in triboelectric charging of the hair, and desirably reduce static charge generation.

What is claimed is:

1. A hair conditioning composition comprising, by weight, based on the total weight of the composition:
a) from 0.1 to 5.0% of a perfluoropolyether selected from the group consisting of perfluoropolymethylisopropylether and polyhexafluoroisopropylether;
b) from 1.0 to 10.0% of a conditioning agent selected from the group consisting of:
  i) amino-functional silicones having an amine content from 0.1 to 1.0 equivalent; and conforming to the formula:

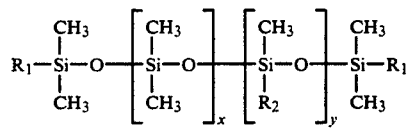

wherein
R₁ is methyl, hydroxy, or methoxy;
R₂ is $(CH_2)_3NH(CH_2)_2NH_2$ or $CH_2CH(CH_3)CH_2NH(CH_2)_2NH_2$;
x and y are integers such that the molecular weight of the polymer ranges from 400–500,000, with the ratio of x/y being such that the amine content ranges from 0.1 to 1.0 equivalent and ii) isothiuronium compounds containing one or more functional groups of the formula:

$$-SC\begin{matrix}\nearrow NH_2^+ \\ \searrow NH_2\end{matrix}$$

and iii) mixtures thereof; and c) the balance being a cosmetically acceptable vehicle.

2. The composition of claim 1, where in the ratio of perfluoropolyether to conditioning agent is from 1:1 to 1:100.

3. The composition of claim 2, wherein the ratio is from 1:1 to 1:10.

4. The composition of claim 1, wherein the perfluoropolyether is perfluoropolymethylisopropylether.

5. The composition of claim 1, wherein the aminofunctional silicone has an amine content from 0.3 to 0.8 equivalent.

6. The composition of claim 1, wherein the silicone is selected from the group consisting of Dow Corning Q2-8220, Dow Corning Q2-8075 and General Electric SF 1708.

7. The composition of claim 1, wherein the silicone is Dow Corning Q2-8220.

8. The composition of claim 1, wherein the isothiuronium compound is selected from the group consisting of

[Structure: bis-isothiuronium compound with CS(CH₂)ₘ and (CH₂)ₘSC groups bonded to N with Alk and CH₂(CH₂)ₙ substituents]

[Structure: $R_1-SC(=NH_2^+Y^-)NH_2$]

[Structure: $R_1-A_a-SC(=NH_2^+Y^-)NH_2$]

[Structure: bis-isothiuronium compound CS—(CH₂)ₓ—A_c—B_d—A_e—SC with NH₂ groups]

-continued

[Structure: $CH_3(CH_2)_nCH_2$—N⁺(Alk)(Alk)—(CH_2)_mSC(=NH_2^+Y^-)NH_2$ with Y⁻]

[Structure: $CH_3(CH_2)_nCH_2$—N⁺(Alk)(Alk)—$CH_2CH_2O(CH_2CH_2O)_pCH_2CH_2SC(=NH_2^+Y^-)NH_2$ with Y⁻]

[Structure: bis-isothiuronium with CS(CH₂)ₒ and (CH₂)ₒSC groups bonded to N⁺(Alk)(Alk)]

wherein
AlK is an alkyl group containing from 1 to 4 carbon atoms;
Y is an anion;
n is an integer from 10 to 24;
m is an integer from 1 to 4;
o is an integer from 8 to 11;
P is an integer from 0 to 20;
with the proviso that the total number of carbon atoms in the cation is not greater than 28; and
compounds having a long alkyl chain interrupted by a phenylene group such that the interrupted alkyl chain conforms to the formula $$CH_3(CH_2)_sCH_2-\phantom{x}\bigcirc\phantom{x}-(CH_2)_t-$$

wherein
s is an integer of 8 to 17; and
t is an integer from 1 to 5; and

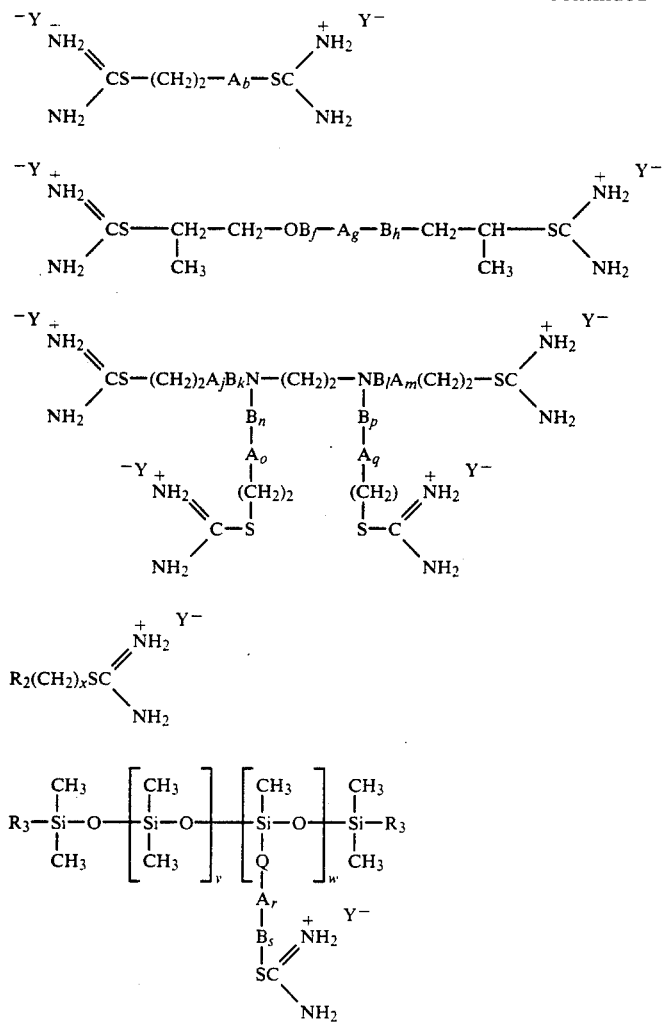

wherein:
  R₁ is an alkyl or arylalkyl group, wherein the alkyl moiety contains from 12 to 24 carbon atoms;
  R₂ is a perfluoroalkyl group having from 4 to 16 carbon atoms;
  R₃ is methyl, hydroxy, or methoxy;
  A is an ethoxy group;
  B is a propoxy group;
  $Y^-$ is an anion; and $Br^-, Cl^-$ or $I^-$
  Q is an alkylene group having from 2 to 5 carbon atoms;
  a through s are integers designating, as the case may be, the degree of ethoxylation and/or propoxylation;
  v is an integer from 5 to 500;
  w is an integer from 5 to 200; and
  n is an integer from 0 to 4.

9. The composition of claim 1, wherein the isothiuronium compound is selected from the group consisting of

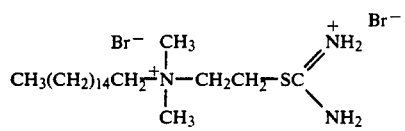

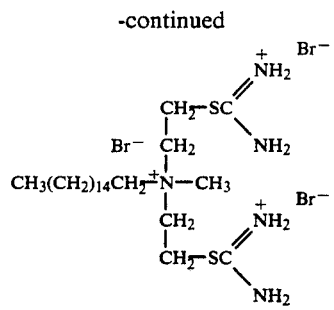

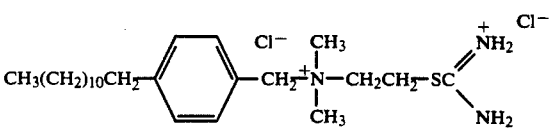

a mixture of compounds of the formula:

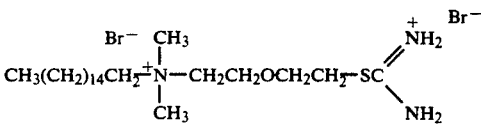

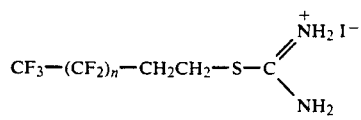

wherein:
n is 3 to 13;

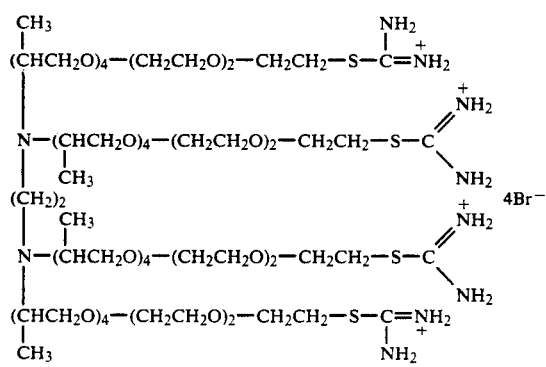

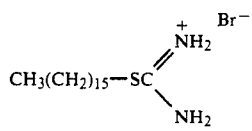

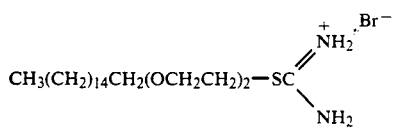

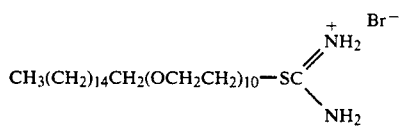

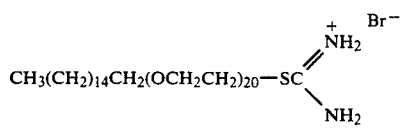

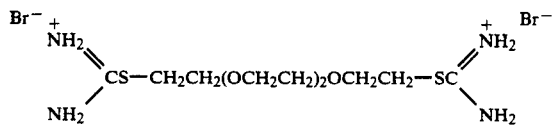

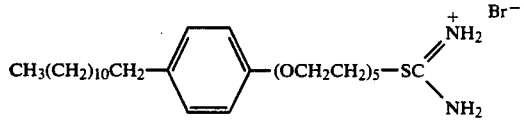

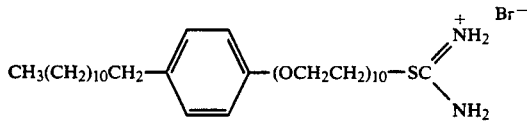

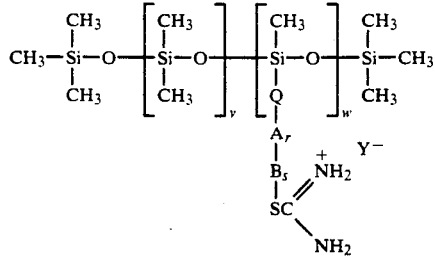

v is an integer of 5 to 500, w is an integer of about 5 to 200; and r and s are integers with values such that the average molecular weight is from about 1000 to about 100,000.

10. The composition of claim 1, wherein the isothiuronium compound is

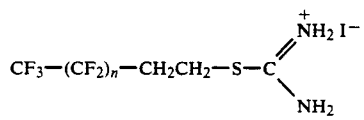

wherein n is an integer of 3 to 13.

11. A process for conditioning hair which comprises contacting the hair with a hair conditioning amount of the composition according to claim 1 for a sufficient time to condition same.

12. The process of claim 11, wherein said contacting is for a period of about 0.5 to 30 minutes.

13. The composition of claim 1, wherein the perfluoropolyether is polyhexafluoroisopropylether.

14. A method of enhancing the hair conditioning effect of a conditioning agent selected from the group consisting of (a) amino-functional silicones having an amine content from 0.1 to 1.0 equivalent and conforming to the formula:

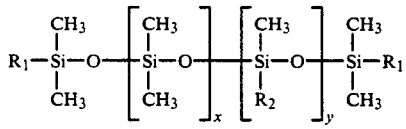

wherein $R_1$ methyl, hydroxy, or methoxy;
wherein $R_2$ is $(CH_2)_3NH(CH_2)_2NH_2$ or $CH_2CH(CH_3)CH_2NH(CH_2)_2NH_2$;
x and y are integers such that the molecular weight of the polymer ranges from 500–500,000, with the ratio of x/y being such that the amine content ranges from 0.1 to 1.0 equivalent;

(b) isothiuronium compounds containing one or more functional groups of the formula:

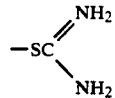

and (c) mixtures thereof said method comprising treating the hair with a conditioning amount of said conditioning agent and a conditioning enhancing amount of a perfluoropolyether selected from the group consisting of perfluroropolymethyl isopropyl ether and polyhexafluoroisopropyl ether.

* * * * *